(12) United States Patent
Chiba et al.

(10) Patent No.: US 9,078,817 B2
(45) Date of Patent: Jul. 14, 2015

(54) OILY SOLID COSMETIC

(75) Inventors: Kiriko Chiba, Yokahama (JP); Fumitaka Sato, Yokahama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 365 days.

(21) Appl. No.: 13/127,003

(22) PCT Filed: Oct. 28, 2009

(86) PCT No.: PCT/JP2009/005687
§ 371 (c)(1),
(2), (4) Date: Jul. 18, 2011

(87) PCT Pub. No.: WO2010/050194
PCT Pub. Date: May 6, 2010

(65) Prior Publication Data
US 2013/0202665 A1 Aug. 8, 2013

(30) Foreign Application Priority Data
Oct. 30, 2008 (JP) .................................. 2008-279151

(51) Int. Cl.
*A61K 8/02* (2006.01)
*A61K 8/25* (2006.01)
*A61K 8/29* (2006.01)
*A61K 8/31* (2006.01)
*A61Q 1/06* (2006.01)
*A61Q 1/02* (2006.01)
*A61Q 1/10* (2006.01)

(52) U.S. Cl.
CPC ................ *A61K 8/022* (2013.01); *A61K 8/025* (2013.01); *A61K 8/0254* (2013.01); *A61K 8/25* (2013.01); *A61K 8/29* (2013.01); *A61K 8/31* (2013.01); *A61Q 1/06* (2013.01); *A61K 2800/412* (2013.01); *A61K 2800/436* (2013.01); *A61K 2800/592* (2013.01); *A61Q 1/02* (2013.01); *A61Q 1/10* (2013.01)

(58) Field of Classification Search
CPC ....... A61K 8/025; A61K 8/0254; A61K 8/25; A61K 8/29; A61K 8/31; A61K 8/022; A61K 2800/412; A61K 2800/436; A61K 2800/592; A61Q 1/06; A61Q 1/02; A61Q 1/10
USPC ........................................................ 424/401
See application file for complete search history.

(56) References Cited

U.S. PATENT DOCUMENTS

| | | | | |
|---|---|---|---|---|
| 6,432,535 | B1 * | 8/2002 | Noguchi et al. | 428/403 |
| 6,482,419 | B1 * | 11/2002 | Miyazaki et al. | 424/401 |
| 6,562,323 | B1 * | 5/2003 | Miyazaki et al. | 424/69 |
| 2005/0129649 | A1 * | 6/2005 | Kurosawa et al. | 424/70.12 |
| 2005/0233015 | A1 * | 10/2005 | Norberg et al. | 424/769 |
| 2006/0062752 | A1 * | 3/2006 | Gotou et al. | 424/70.31 |

FOREIGN PATENT DOCUMENTS

| | | | |
|---|---|---|---|
| EP | 0905206 | A2 * | 3/1999 |
| EP | 0919599 | A2 * | 6/1999 |
| JP | 6-279235 | | 10/1994 |
| JP | 11-236315 | | 8/1999 |
| JP | 2001-2921 | | 1/2001 |
| JP | 2004-517092 | | 6/2004 |
| JP | 2005-289971 | | 10/2005 |
| JP | 2006-273769 | | 10/2006 |
| JP | 2006-306829 | | 11/2006 |

OTHER PUBLICATIONS

Japanese Office Search Report for PCT/JP2009/005687 filed Oct. 28, 2009, (both JP and English 4 pages).
JPO Patent Gazette (JP B-4562791) certificate of translation, publication, and complete translation (43 pages).
JPO Decision to Grant a Patent (JP 2008-279151), certificate of translation, JP version, and complete translation (7 pages).
JPO Written Amendment (JP 2008-279151), certificate of translation, JP version, and complete translation (3 pages).
JPO Written Argument (JP 2008-279151), certificate of translation, JP version, and complete translation (17 pages).
JPO Notice of Reasons for Rejection (JP2008-279151), certificate of translation, JP version, and complete translation (9 pages).
JPO 2008-279151, certificate of translation and complete translation (29 pages).

* cited by examiner

*Primary Examiner* — Anoop Singh
*Assistant Examiner* — Doan Phan
(74) *Attorney, Agent, or Firm* — Andrew F. Young, Esq.; Lackenbach Siegel, LLP

(57) ABSTRACT

An oily solid cosmetic is capable of effectively diminishing morphological problems, such as vertical wrinkles, in particular on the lip, over a long period of time. The present invention provides an oily solid cosmetic which contains: (A) a plate-like composite powder presenting interference colors, (B) a spherical composite powder wherein the surface of a spherical powder having a refractive index of 1.40 to 1.60 is coated with a coating component having a refractive index of 2.00 to 2.90, and (C) 1 to 40% by mass of a semi-solid oil component. Preferably, the cosmetic of the present invention further contains (D) heavy isoparaffin. The cosmetic of the present invention is capable of diminishing vertical wrinkles, in particular on the lip, over a long period of time, and of maintaining a glossy lip.

3 Claims, 1 Drawing Sheet

(A)
(B)
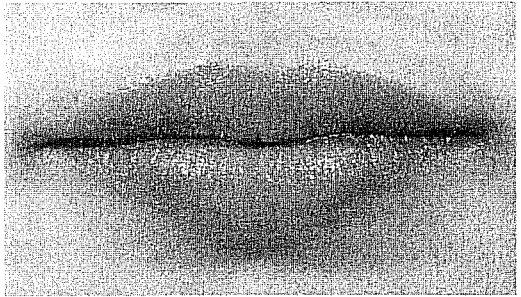
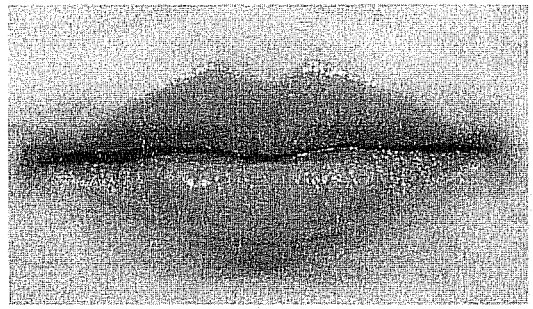

OILY SOLID COSMETIC

CROSS REFERENCE TO RELATED APPLICATIONS

This application relates to and claims priority from PCT/JP2009/005687 filed Oct. 28, 2009, the entire contents of which are incorporated herein by reference, which in turn claims priority from JP 2008-279151 filed Oct. 30, 2008, granted as JP Pat No. JP 4562791 on Aug. 6, 2010.

BACKGROUND OF THE INVENTION

1. Field of the Invention

The present invention relates to an oily solid cosmetic excellent in a wrinkle-concealing effect. More specifically, the present invention relates to an oily solid cosmetic which is formulated with a plate-like composite powder and a spherical composite powder in combination and further contains a semi-solid oil component to successfully diminish vertical wrinkles on the skin, in particular on the lip, over a long period of time.

2. Description of the Related Art

It is one of the main effects of makeup cosmetics such as foundation and lipstick to cover morphological problems such as wrinkles, follicles, roughness of the skin, and blotches.

Patent Document 1 describes that an excellent effect of covering morphological problems can be acquired by applying a makeup base (the first layer) containing sticky substances and then overlaying a finishing cosmetic (the second layer) which contains a powder presenting diffuse reflection of light thereon. The powder presenting diffuse reflection which is contained in the finishing cosmetic (the second layer) specifically contains inorganic particles such as silicon dioxide, aluminum silicate, titanium dioxide-coated mica, and montmorillonite particles, and organic particles such as nylon powder, methyl methacrylate powder, and polyethylene powder particles. For acquiring the desired continuous covering effect, however, the technique described in Patent Document 1 requires a step of overlayering a finishing cosmetic on a makeup base.

Although Patent Document 1 describes that either of a plate-like powder and a spherical powder can be used as the powder presenting diffuse reflection of light, there has been a problem that, if a spherical resin powder (such as nylon powder) having a modifying effect for diminishing roughness of the skin, follicles, and the like is formulated in combination with a plate-like pearl agent (titanium dioxide-coated mica, for example) in a cosmetic, for example, the modifying effect provided by the spherical resin powder and the gloss provided by the pearl agent are balanced out to be inadequate.

On the other hand, various spherical pearlescent agents which compensate for a drawback of a flake-like or a plate-like pearl agent as used in Patent Document 1 and provide a smooth texture have been developed, and a cosmetic formulated with such a spherical pearlescent agent is thought to be able to improve morphological problems of the skin such as wrinkles, and tone problems such as spots, freckles, and dullness of the skin (Patent Documents 2 and 3). The cosmetics described in Patent Documents 2 and 3 are base makeup cosmetics such as foundation and have an effect of providing lucency to the skin and improving morphological/tone problems; however, such a spherical pearlescent agent never been reported to be formulated in an oily solid cosmetic, in particular a lipstick, and its effect of diminishing vertical wrinkles on the lip has not been identified.

Patent Document 4 discloses a powder (including plate-like powder and spherical powder) having a plurality of layers (preferably three or more layers) of coatings with different refractive indices and describes that a powder having a desired saturation and brightness is obtained by constituting at least one of the plurality of layers of an aggregate of crystallized microparticles to generate diffusion and reflection of light between the surface of and a space. Patent Document 4 also illustrates oily cosmetics such as a lipstick and an eyeliner formulated with such a powder.

PRIOR ART PUBLICATIONS

Patent Document

Patent Document 1: JP-A-Hei 6-128122
Patent Document 2: JP-A-2003-55573
Patent Document 3: JP-A-2000-319540
Patent Document 4: JP-A-2001-302432

ASPECTS AND SUMMARY OF THE INVENTION

Problems to be Solved by the Invention

Although a base makeup cosmetic such as a foundation formulated with a conventional pearl agent (pearlescent agent) can improve morphological problems or tone problems of the skin, an oily solid makeup cosmetic, in particular a lipstick, formulated with the conventional pearl agent does not have an adequate effect of diminishing vertical wrinkles on the lip.

Means for Solving the Problems

The present inventors have made intensive researches to solve these problems and found that formulating a cosmetic with a plate-like composite powder and a spherical composite powder, and further a predetermined amount of a semi-solid oil makes it possible to diminish vertical wrinkles on the lip over a long period of time and furthermore to maintain a glossy lip, and thus accomplished the present invention.

Thus, the present invention provides an oily solid cosmetic which contains (A) a plate-like composite powder presenting interference colors, (B) a spherical composite powder comprising a spherical powder having a refractive index of 1.40 to 1.60 whose surface is coated with a coating component having a refractive index of 2.00 to 2.90, and (C) 1 to 40% by mass of a semi-solid oil component.

Effects of the Invention

The cosmetic of the present invention can exhibiting a desired effect by application once, diminishes vertical wrinkles, in particular on the lip, and provides a glossy lip, and these effects last over a long period of time.

The above, and other aspects, features and advantages of the present invention will become apparent from the following description read in conjunction with the accompanying drawings, in which like reference numerals designate the same elements.

BRIEF DESCRIPTION OF THE DRAWINGS

FIG. 1A is a photograph showing a comparison of the lip applied with the cosmetic of Comparative Example 3 containing only a plate-like composite powder; and FIG. 1B a photograph of the lip applied with the cosmetic of the present invention (Example 1).

DETAILED DESCRIPTION OF THE PREFERRED EMBODIMENTS

Reference will now be made in detail to embodiments of the invention that are illustrated in the discussion herein.

Embodiments for Carrying out the Invention

The plate-like composite powder used in the present invention is a plate-like powder presenting interference colors, and although those generally used in cosmetics can be used, a plate-like laminate, also referred to as a pearl agent, presenting interference colors is particularly preferable. It has an effect of emitting a strong light from a metal oxide layer referred to as an interference layer. A plate-like composite powder composed of a laminate of a plurality of materials having a refractive index difference of particularly 0.3 to 2, and preferably 0.5 to 1.7 is suitably used.

Specifically, for example, titanated mica, red iron oxide-coated mica, red iron oxide-coated titanated mica, carmine-coated titanated mica, prussian blue-coated titanated mica, titanium oxide-coated synthetic phlogopite, red iron oxide/titanium oxide-coated synthetic phlogopite, titanium oxide-coated glass flakes, titanium oxide-coated alumina flakes (XIRONA SILVER manufactured by Merck Ltd., for example), titanium oxide-coated silica flakes (XIRONA MAGIC MAUVE manufactured by Merck Ltd., for example), iron oxide/silica-coated aluminum, iron oxide/silica-coated iron oxide, titanium oxide and silicon oxide-coated mica (TIMIRON SPLENDID GOLD and XIRONA CARIBBEAN BLUE manufactured by Merck Ltd., for example), titanium oxide-coated glass flakes (METASHINE MC1080RR manufactured by Nippon Sheet Glass Co., Ltd., REFLEX Series manufactured by Engelhard Corporation, for example) can be used.

The average particle size of the plate-like composite powder is preferably 5 µm to 30 µm. The average particle size not larger than 5 µm may provide an insufficient color expression, and the diameter not smaller than 30 µm may provide an increased glare to emphasize the contrast of wrinkles.

The spherical composite powder used in the present invention is a spherical powder wherein the surface of a spherical powder having a refractive index of 1.40 to 1.60 is coated with a coating component having a refractive index of 2.00 to 2.90, and the composite powder described in Japanese Patent Laid-Open No. 11-236315 is particularly preferred. Such a spherical composite powder enables a spherical particle to present colors resulting from interference colors, which has been considered to be difficult for spherical particles, and also solved problems as for an excessive luster and usability of a plate-like powder by using spherical particles preferably with the same particle size as a core and setting refractive indices of both the spherical particle and a coating component coating thereon within the above range.

Specific examples and the production method of the spherical composite powder used in the present invention are described in detail in JP-A-Hei 11-236315. In brief, the spherical composite powder is produced by using a spherical particle composed of a material having a refractive index of 1.40 to 1.60 (preferably with a particle size of 2.0 µm to 50.0 µm) as a particle to serve as its core (a core particle), and coating the core particle with a coating component having a refractive index of 2.00 to 2.90 as a film.

The material constituting the core particle includes inorganic and organic materials such as silicon dioxide, alumina, calcium carbonate, barium sulfate, nylon, polyethylene, polystyrene, and polymethyl methacrylate. As the core particle, for example, a spherical particle granulated using a CF-granulator and the like, or commercially available spherical particles can be sued.

The coating component includes titanium dioxide, a particular low-dimensional titanium oxide (titanium oxide having an oxidation degree of titanium lower than that of titanium dioxide ($TiO_2$), for example, $Ti_2O$, $TiO$, $Ti_2O_3$, $Ti_3O_5$, $Ti_4O_7$, and the like), zinc oxide, zirconium oxide, iron oxide, and the like.

Among them, a coating component having silicon dioxide as its core particle coated with titanium dioxide is particularly preferred due to its excellent effect of diminishing vertical wrinkles on the lip. The coating may be a multilayer, for example, titanium dioxide/silica/titanium dioxide.

The thickness of a coating in a spherical composite powder is preferably within the range of about 190 to 780 nm as an optical film thickness (a geometrical film thickness X a refractive index). The interference color presented by the spherical composite powder varies depending on a material used as a core particle or a coating component, the ratio by weight of the core particle and the coating component, and the like, and these conditions may be appropriately adjusted in accordance with the desired interference color.

The particle size of the spherical composite powder used in the cosmetic of the present invention is preferably 2 to 20 µm, and more preferably 4 to 15 µm. A spherical composite powder having a particle size smaller than 0.5 µm may cause a scratchy feel at the time of using a cosmetic containing the spherical composite powder, and that having a particle size of larger than 20 µm tends to render the surface applied with the cosmetic rough.

The formulation amount of the composite powder in the cosmetic of the present invention is not more than 20% for the plate-like composite powder and not more than 15% for the spherical composite powder, preferably 1 to 15% for the plate-like composite powder and 1 to 12% for the spherical composite powder, and more preferably within the range of 2 to 10% for the plate-like composite powder and within the range of 1 to 10% for the spherical composite powder. The formulation amount (%) of the composite powder in the present specification is in % by mass, unless otherwise indicated.

The formulation ratio of the plate-like composite powder to the spherical composite powder in the cosmetic of the present invention is preferably within the range of 5:1 to 1:2, and more preferably within the range of 3:1 to 1:1. The formulation ratio beyond the above range renders the effect of covering wrinkles and the like, which is the purpose of the present invention, inadequate. Particularly, when an excessive amount of the plate-like composite powder is formulated, the stretching smoothness and the gloss of the cosmetic tend to decrease.

The cosmetic of the present invention contains a predetermined amount of a semi-solid oil in addition to the plate-like composite powder and the spherical composite powder. The semi-solid oil used in the present invention is an oil component having a melting point of 30 to 52° C., more preferably 30 to 45° C., and refers to a semi-solid oil having a hardness at 25° C. of 0.1 to 10 N.

The melting point in the present specification is the value measured as follows. That is, a sample is firstly gradually heated to 90 to 92° C. while thoroughly stirred to be melted and, after heating is stopped, the sample is left to cool to the temperature higher by 8 to 10° C. than its melting point. Then, a thermometer (a thermometer defined in Japanese Industrial Standards B7410 for measuring a melting point of petrolatum) is cooled to 5° C., moisture is wiped out from it using a filter paper, the thermometer is inserted into the sample as deep as halfway of the mercury bulb, then immediately taken out, and left to cool while vertically maintained and, when the sample adhering to the thermometer begins to turn to turbid, the thermometer is immersed in water at a temperature of not higher than 16° C. for 5 minutes. Then, the thermometer is inserted in a test tube (25×100 mm) and immobilized by using cork so that the distance between the lower end of the thermometer and the bottom of the test tube is 15 mm. The test tube is immobilized in a 500 mL beaker containing water at about 16° C. so that the distance between the bottom of the test tube and the bottom of the beaker is 15 mm, and heated so that the temperature in a bath increases by 2° C. in one minute until the temperature reaches 30° C. After that, heating is continued so that the temperature increases by 1° C. in one minute and the temperature at the time when one drop of the sample drops from the thermometer is measured. This measurement is carried out three times and, when the differences between measurements are smaller than 1° C., a melting point is determined to be the average value of them, or when the differences between measurements are not smaller than 1° C., this measurement is carried out five times in total and a melting point is determined to be the average value of them.

The hardness in the present specification is the value measured using a rheometer manufactured by Leotec Co., Ltd. with a plunger of 5φ, a penetration speed of a needle of 2 cm/min, and a penetration depth of a needle of 3 mm. The semi-solid oil of the present invention thus does not include an oil which is hard at room temperature, for example, a liquid oil with a high viscosity such as polybutene, hydrogenated castor oil, and hard lanolin.

As the semi-solid oil of the present invention, in addition to lanoline, vegetable oils such as shea butter, partially hydrogenated coconut oil and partially hydrogenated jojoba oil, which are usually used in cosmetics, pentaerythrite tetra(behenate/benzoate/ethylhexanoate), macadamia seed oil polyglyceryl-6-esters behenate, phytosteryl/behenyl dimer dilinoleate, dipentaerythrityl hexahydroxystearate, and the like.

These semi-solid oils may be commercially available products, and include the followings, for example: "COSMOL 168EV/M/AR", "SALACOS P-B822" (both of these are manufactured by Nisshin OilliO Group, Ltd.), "S FACE VL-211" (manufactured by Sakamoto Yakuhin Kogyo Co., Ltd.), "YOFCO-MAS", "Plandool-S/H/G/PB" (both of these are manufactured by NIPPON FINE CHEMICAL CO., LTD.), "SOFTISAN649" (manufactured by Sasol Limited), "Eldew PS-304" (manufactured by Ajinomoto).

The formulation amount of the semi-solid oil is 1 to 40% by mass, more preferably 5 to 30% by mass, and even more preferably 10 to 20% by mass, relative to the total weight of cosmetic. The formulation amount of less than 1% by mass cannot provide an effect of covering wrinkles over time, and the formulation amount of more than 40% by mass deteriorates the smoothness of the cosmetic formulated with the semi-solid oil.

The cosmetic of the present invention is formulated with a combination of the plate-like composite powder and the spherical composite powder as well as the predetermined amount of the semi-solid oil so that it has an excellent effect of covering vertical wrinkles, in particular on the lip, and the effect lasts over a long period of time. The oily solid cosmetic of the present invention is thus suitable as a cosmetic for the lip such as a lipstick, a lip gloss, and a lip balm, and exhibits an excellent effect as a lipstick in particular.

By formulating heavy liquid isoparaffin in the cosmetic of the present invention, the stretching smoothness upon application can be further improved. When heavy liquid isoparaffin is formulated, its formulation amount is 1 to 50% by mass, and more preferably 10 to 30% by mass.

The cosmetic of the present invention can be formulated with various coloring materials. Examples of the coloring material preferably used include inorganic coloring pigments such as titanium oxide, iron oxide (red iron oxide), yellow iron oxide, Blue No. 1 aluminum lake, titanium dioxide, and zinc oxide, inorganic red pigments such as titanium iron oxide, inorganic brown pigments such as γ-iron oxide, inorganic yellow pigments such as ochre, inorganic black pigments such as black iron oxide, carbon black, and low-dimensional titanium oxide, inorganic violet pigments such as mango violet and cobalt violet, inorganic green pigments such as chromium oxide, chromium hydroxide and cobalt titanium oxide, inorganic blue pigments such as ultramarine and prussian blue, and organic pigments containing zirconium or barium such as Red No. 201, Red No. 202, Red No. 204, Red No. 205, Red No. 220, Red No. 226, Red No. 228, Red No. 305, Orange No. 203, Orange No. 204, Yellow No. 205, Yellow No. 401, Blue No. 404, as well as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1, and the surface of these may be treated with silicone or the like.

The cosmetic of the present invention can be optionally formulated with, in addition to the components mentioned above, components which can be usually formulated in cosmetics as long as these components do not impair the use of the cosmetic and the effect which the cosmetic intends to exhibit. Examples of such a component include a liquid oil component (except heavy liquid isoparaffin), a solid oil component, a powder material, and the like. These examples are, however, by no means limitative of the scope of the invention.

Examples of the liquid oil component include liquid paraffin, squalane, a lanoline derivative, higher alcohol, various ester oils, silicone oil, polyalkylene glycol polyether, and the like carboxylic acids, an oligoester compound, terpene hydrocarbon oil, and the like.

The solid oil component includes a wax having a melting point of not lower than 60° C., preferably having a melting point of not lower than 65° C., for example, ceresin wax, carnauba wax, polyethylene wax, paraffin wax, Fischer-Tropsch Wax, candelilla wax, microcrystalline wax, behenic acid, behenyl alcohol, Japan wax, rice wax, beeswax, cetanol, and the like.

Among them, hydrocarbon wax is preferred, and polyethylene wax, microcrystalline wax and paraffin wax are particularly preferred. The formulation amount of the solid oil component is preferably 5 to 30%, and particularly preferably 10% to 25%.

Examples of the powder material include inorganic powders such as talc, kaolin, sericite (sericite), muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, a metal tungstate, magnesium, silica, zeolite, bentonite, barium sulfate, calcined calcium sulfate (calcined plaster), calcium phosphate, fluorapatite, hydroxyapatite, a ceramic powder, boron nitride, titanium dioxide, and zinc oxide, organic powders such as a polyamide resin powder, a nylon powder, a polyethylene powder, a polypropylene powder, a polyester powder, a polymethyl methacrylate powder, a polystyrene powder, a styrene/acrylic acid copolymer resin powder, a silicone resin powder, a benzoguanamine resin powder, a polytetrafluoroethylene powder, and a cellulose powder, various pigments, and the like.

Other than above mentioned, a dispersant, a surfactant, a thickener, a gelling agent, an antioxidant, an ultraviolet absorber, an ultraviolet blocker, a preservative, a moisturizer, a dye, various agents, and the like can be formulated, for example.

Examples

The present invention will be described in detail below with reference to Examples, but the present invention is not limited to these Examples. The formulation amount in the following Examples and the like is in % by mass, unless otherwise indicated.

Preparation Example

A spherical composite powder containing a spherical particle of silicon dioxide as its core particle and titanium dioxide as a coating component was produced as follows.

The commercially available spherical silicon dioxide (average particle size of about 5 μm, refractive index of 1.46: manufactured by AGC Si-Tech Co., Ltd.) was dispersed in water, 1% by weight of stannic chloride (manufactured by Wako Pure Chemical Industries, Ltd.) was added dropwise thereto, and the mixture was subjected to hydrolysis while heated. Then, a titanium tetrachloride solution (concentration of 16%: manufactured by Wako Pure Chemical Industries, Ltd.) obtained by dissolving 100 parts of spherical silicon dioxide and 80 parts of titanium dioxide in water was added dropwise thereto, and the mixture was subjected to hydrolysis while heated. After the completion of the reaction, filtration and drying were conducted and the product was calcined at 800° C. for 3 hours to provide a spherical composite powder having silicon dioxide coated with 80% of rutile-type titanium oxide (refractive index of 2.5 to 2.7), an average particle size of about 6 μm, and a red interference color.

Examples and Comparative Examples

Each component in the compositions listed in the following Tables 1 and 2 was fused at 90 to 100° C. while heated, mixed while stirred, deaerated, and cooled to prepare a stick-type cosmetic (lipstick). In the Tables, titanium oxide-coated mica (FLAMENCO RED manufactured by BASF, having an average particle size of about 20 μm) was used as the plate-like composite powder, and the powder prepared above was used as the spherical composite powder.

As for the cosmetics (lipstick) in Examples 1 to 6 and Comparative Examples 1 to 4, a panel of six experts actually used (applied) each lipstick and evaluated it for each of the following evaluation items in accordance with the following evaluation criteria. As for the level of pearly shininess of color, Good should be given when saturation/brightness is moderate and an evaluation lower than Good should be given when saturation/brightness is too high or too low.

<Evaluation Items>
level of diminishing wrinkles on the lip immediately after application (effect of covering wrinkles)
stretching smoothness upon application
gloss immediately after application
level of pearly shininess of color immediately after application
gloss over time (two hours after application)
level of diminishing wrinkles on the lip over time (two hours after application)

<Evaluation Criteria (Evaluation in Five Stages)>
5: Very Good
4: Good
3: Average
2: Poor
1: Very Poor After evaluation results obtained were summed up and then averaged for each item, the values obtained were classified into the following index levels, characters for which are shown in Table 1.

<Indices for Evaluation Results>
A: average value of not less than 4.5
B: average value of not less than 3.5 but less than 4.5
C: average value of not less than 2.5 but less than 3.5
D: average value of not less than 1.5 but less than 2.5
E: average value of not less than 1.0 but less than 1.5

TABLE 1

|  | Example 1 | Example 2 | Example 3 | Example 4 | Example 5 | Example 6 |
| --- | --- | --- | --- | --- | --- | --- |
| Polyethylene wax (average molecular weight of 500) | 10 | 10 | 10 | 10 | 10 | 10 |
| Microcrystalline wax | 5 | 5 | 5 | 5 | 5 | 5 |
| Paraffin | 5 | 5 | 5 | 5 | 5 | 5 |
| Heavy liquid isoparaffin | — | — | — | 20 | 20 | 20 |
| Pentaerythrityl tetra(behenate/benzoate/ethylhexanoate) | 10 | 2 | 38 | 10 | 10 | 10 |
| Diisostearyl malate | 15 | 15 | 15 | 15 | 15 | 15 |
| Methylphenyl polysiloxane | Remainder | Remainder | Remainder | Remainder | Remainder | Remainder |
| Plate-like composite powder | 3 | 3 | 3 | 3 | 5 | 2 |
| Spherical composite powder | 3 | 3 | 3 | 3 | 1 | 4 |

TABLE 1-continued

|  | Example 1 | Example 2 | Example 3 | Example 4 | Example 5 | Example 6 |
|---|---|---|---|---|---|---|
| Titanium oxide | 2 | 2 | 2 | 2 | 2 | 2 |
| Iron oxide | 3 | 3 | 3 | 3 | 3 | 3 |
| Yellow iron oxide | 3 | 3 | 3 | 3 | 3 | 3 |
| Blue No. 1 aluminum lake | 1 | 1 | 1 | 1 | 1 | 1 |
| Red No. 202 | 1 | 1 | 1 | 1 | 1 | 1 |
| Tocopherol | 0.1 | 0.1 | 0.1 | 0.1 | 0.1 | 0.1 |
| Methoxycinnamate | 1 | 1 | 1 | 1 | 1 | 1 |
| Level of diminishing wrinkles on the lip | A | B | A | A | B | A |
| Stretching smoothness upon application | A | A | B | A | A | A |
| Gloss upon application | B | B | A | A | A | B |
| Level of pearly shininess of color | A | A | A | A | A | B |
| Gloss over time | A | B | A | A | A | B |
| Level of diminishing wrinkles on the lip over time | A | B | A | A | B | A |

TABLE 2

|  | Comparative Example 1 | Comparative Example 2 | Comparative Example 3 | Comparative Example 4 |
|---|---|---|---|---|
| Polyethylene wax (average molecular weight of 500) | 10 | 10 | 10 | 10 |
| Microcrystalline wax | 5 | 5 | 5 | 5 |
| Paraffin | 5 | 5 | 5 | 5 |
| Heavy liquid isoparaffin | — | — | — | — |
| Pentaerythrityl tetra(behenate/benzoate/ethylhexanoate) | 0.5 | 45 | 10 | 10 |
| Diisostearyl malate | 15 | 15 | 15 | 15 |
| Methylphenyl polysiloxane | Remainder | Remainder | Remainder | Remainder |
| Plate-like composite powder | 3 | 3 | 3 | — |
| Spherical composite powder | 3 | 3 | — | 3 |
| Titanium oxide | 2 | 2 | 2 | 2 |
| Iron oxide | 3 | 3 | 3 | 3 |
| Yellow iron oxide | 3 | 3 | 3 | 3 |
| Blue No. 1 aluminum lake | 1 | 1 | 1 | 1 |
| Red No. 202 | 1 | 1 | 1 | 1 |
| Tocopherol | 0.1 | 0.1 | 0.1 | 0.1 |
| Methoxycinnamate | 1 | 1 | 1 | 1 |
| Level of diminishing wrinkles on the lip | B | A | E | D |
| Stretching smoothness upon application | A | E | A | A |
| Gloss upon application | D | A | B | A |
| Level of pearly shininess of color | A | A | A | E |
| Gloss over time | D | A | A | A |
| Level of diminishing wrinkles on the lip over time | E | A | E | D |

Shown in FIG. 1 are photographs indicating the result of comparison between lips each of which was applied with the lipstick of Comparative Example 3 or Example 1. Although, on the lip (A) applied with the lipstick of Comparative Example 3 containing only a plate-like composite powder but not being formulated with a spherical composite powder, wrinkles (in particular vertical wrinkles) which had been seen before application were emphasized, on the lip (B) applied with the lipstick of Example 1, wrinkles on the lip were diminished.

Formulation Example 1

Eye Shadow

<Production Method>
Each composition was mixed at 80° C. and poured into a mold to cool solidify it to prepare a product.

| Component | Amount (% by mass) |
|---|---|
| Spherical composite powder | 5 |
| Plate-like composite powder | 2 |
| Pentaerythrityl tetra(behenate/benzoate/ethylhexanoate) | 5 |
| Heavy liquid paraffin | 10 |
| Ceresin | 1 |
| Decamethylcyclopentasiloxane | Remainder |
| Polyoxyethylene/methylpolysiloxane copolymer | 2 |
| Macadamia seed oil | 1 |
| Sorbitan sesquiisostearate | 2 |
| Synthetic phlogopite | 0.1 |
| Mica | 30 |
| Black iron oxide-coated titanated mica (pearl agent) | q.s. |
| D-δ-tocopherol | q.s. |
| Ultramarine pink | 1 |
| Dimethyl distearyl ammonium hectorite | 3 |
| Trimethylsiloxysilicate | 3 |
| Perfume | q.s. |

Formulation Example 2

Eye Shadow

<Production Method>
Oil components and waxes were stirred while heated at 95° C. to uniform consistency, and compositions other than oil components were stirred at a room temperature to uniform consistency. The heated oil components were added to the latter mixture, and the obtained mixture was poured into a mold to be pressed to produce a product.

| Component | Amount (% by mass) |
| --- | --- |
| Spherical composite powder | 5 |
| Plate-like composite powder | 2 |
| Pentaerythrityl tetra(behenate/benzoate/ethylhexanoate) | 5 |
| Heavy liquid paraffin | 10 |
| Petrolatum | 2 |
| Methylphenyl polysiloxane | 2 |
| Glycerol | 0.1 |
| Trioctanoin | 1 |
| Vegetable squalane | 0.5 |
| Sorbitan sesquiisostearate | 1 |
| Alkyl-modified silicone resin-coated red iron oxide | 0.1 |
| Boron nitride | 2 |
| Titanated mica | 4 |
| Phlogopite | 4 |
| Synthetic phlogopite | 0.1 |
| Sericite | 20 |
| Talc | Remainder |
| Mica | 7 |
| Zinc myristate | 1 |
| Aluminum stearate | 0.01 |
| Silicic anhydride | 4 |
| Phytosterol | 0.01 |
| DL-α-tocopherol | 0.02 |
| Sodium acetylated hyaluronate | 0.02 |
| P-hydroxybenzoic acid ester | 0.2 |
| Red iron oxide | 7 |
| Black iron oxide | 2 |
| Synthetic sodium/magnesium silicate | 0.1 |
| Perfume | q.s. |
| Diisostearyl malate | 5 |
| Triisostearate | 2 |

Formulation Example 3

Mascara

| Component | Amount (% by mass) |
| --- | --- |
| Spherical composite powder | 5 |
| Plate-like composite powder | 2 |
| Pentaerythrityl tetra(behenate/benzoate/ethylhexanoate) | 5 |
| Heavy liquid paraffin | 15 |
| Dimethylpolysiloxane | 2 |
| Decamethylcyclopentasiloxane | 10 |
| Trimethylsiloxysilicate | 10 |
| Methylpolysiloxane emulsion | q.s. |
| 1,3-butylene glycol | 4 |
| Polyethylene glycol dioleate | 2 |
| Diglyceryl diisostearate | 2 |
| Sodium hydrogen carbonate | 0.2 |
| DL-α-tocopherol acetate | 0.1 |
| P-hydroxybenzoic acid ester | q.s. |
| Sodium dehydroacetate | q.s. |
| Black iron oxide | 7 |
| Bentonite | 1 |
| Dimethyl distearyl ammonium hectorite | 6 |
| Polyvinyl acetate emulsion | 30 |
| Purified water | Remainder |

Formulation Example 4

Foundation

| Component | Amount (% by mass) |
| --- | --- |
| Spherical composite powder | 5 |
| Plate-like composite powder | 2 |
| Pentaerythrityl tetra(behenate/benzoate/ethylhexanoate) | 5 |
| Heavy liquid paraffin | 10 |
| Polymethylhydrogensiloxane | 0.5 |
| Sorbitan sesquiisostearate | 1 |
| Decamethylcyclopentasiloxane | Remainder |
| Rice wax | 7 |
| Calcium hydrogen phosphate | 3 |
| Yellow iron oxide | 2 |
| Red iron oxide | 1 |
| Black iron oxide | q.s. |
| Titanium oxide | 8 |
| Talc | 5 |
| Barium sulfate | 2 |
| Calcined sericite | 10 |
| DL-α-tocopherol acetate | 0.1 |
| 2-ethylhexyl p-methoxycinnamate | 3 |
| Silicic anhydride | 5 |

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. An oily solid cosmetic, comprising:
   (A) plate-like composite powder having a single coating layer presenting interference colors selected from the group consisting of titanated mica, red iron oxide-coated mica, titanium oxide-coated synthetic phlogopite, titanium oxide-coated glass flakes, titanium oxide-coated alumina flakes, and titanium oxide-coated silica flakes;
   (B) spherical composite powder comprising a spherical powder having a refractive index of 1.40 to 1.60 and a particle size range of 2 to 20 μm, whose surface is coated with a coating component having a refractive index of 2.00 to 2.90; and
   (C) 1 to 40% by mass of a semi-solid oil component having a melting point of 30 to 52° C. and having a hardness at 25° C. of 0.1 to 10 N.

2. The oily solid cosmetic according to claim 1, further comprising (D) heavy liquid isoparaffin.

3. The cosmetic according to claim 1, wherein the ratio of the plate-like composite powder to the spherical composite powder is within the range of 5:1 to 1:2.

* * * * *